United States Patent
Chen et al.

(10) Patent No.: US 10,898,616 B1
(45) Date of Patent: Jan. 26, 2021

(54) PEELABLE HEAT-SHRINK TUBING

(71) Applicant: TELEFLEX MEDICAL INCORPORATED, Morrisville, NC (US)

(72) Inventors: Jiunn-Yow Chen, Amherst, NH (US); Mark Croteau, Swanzey, NH (US)

(73) Assignee: TELEFLEX MEDICAL INCORPORATED, Morrisvile, NC (US)

( * ) Notice: Subject to any disclaimer, the term of this patent is extended or adjusted under 35 U.S.C. 154(b) by 194 days.

(21) Appl. No.: 16/032,448

(22) Filed: Jul. 11, 2018

Related U.S. Application Data

(60) Provisional application No. 62/531,228, filed on Jul. 11, 2017.

(51) Int. Cl.
*A61L 29/04* (2006.01)
*A61M 25/10* (2013.01)
(Continued)

(52) U.S. Cl.
CPC ......... *A61L 29/04* (2013.01); *A61M 25/0012* (2013.01); *A61M 25/0023* (2013.01);
(Continued)

(58) Field of Classification Search
CPC ......... B29C 48/09; B29C 65/02; B29C 65/74; B29C 66/40; A61M 25/0009; A61M 25/0023; A61M 25/0045; C08L 27/12; A61L 29/041; A61L 29/049; B29K 2023/10; B29K 2995/0049;
(Continued)

(56) References Cited

U.S. PATENT DOCUMENTS

| 4,251,305 A | 2/1981 | Becker et al. |
| 4,325,998 A | 4/1982 | Chapman |

(Continued)

FOREIGN PATENT DOCUMENTS

| JP | S54142277 A | 11/1979 |
| JP | S60227314 A | 11/1985 |

(Continued)

*Primary Examiner* — Yan Lan
(74) *Attorney, Agent, or Firm* — BakerHostetler

(57) ABSTRACT

A peelable heat-shrink tubing includes a base polymer comprising fluorinated ethylene propylene (FEP), and at least one fluoropolymer coextruded with the base polymer. The peelable heat-shrink tubing may have a haze between about 40% and 80%, inclusive, and/or a total luminous transmittance between about 70% and 85%, inclusive. In some embodiments, the haze may be between about 50% and 70%, inclusive, and/or the total luminous transmittance may be less than about 80%. The base polymer may comprise FEP NP-130 and constitute between about 87.5% and 92.5% by composition of the peelable heat-shrink tubing, inclusive, and the at least one fluoropolymer may comprise ethylene tetrafluoroethylene (ETFE) and constitute between about 7.5% and 12.5% by composition of the peelable heat-shrink tubing, inclusively. In some embodiments, the at least one fluoropolymer may comprise 7.5% of ETFE and 5% of perfluoroalkoxy alkane (PFA), each by composition of the peelable heat-shrink tubing, inclusive.

17 Claims, 2 Drawing Sheets

(51) Int. Cl.
*B65D 71/08* (2006.01)
*F16L 11/04* (2006.01)
*B29C 65/02* (2006.01)
*A61M 25/00* (2006.01)
*B29C 65/00* (2006.01)
*B65B 53/02* (2006.01)
*B29C 65/74* (2006.01)
*B29C 48/09* (2019.01)
*B29L 23/00* (2006.01)
*B29K 23/00* (2006.01)

(52) U.S. Cl.
CPC .......... *A61M 25/0045* (2013.01); *B29C 48/09* (2019.02); *B29C 65/02* (2013.01); *B29C 65/74* (2013.01); *B29C 66/40* (2013.01); *B65B 53/02* (2013.01); *B65D 71/08* (2013.01); *F16L 11/04* (2013.01); *B29K 2023/10* (2013.01); *B29K 2995/0049* (2013.01); *B29L 2023/22* (2013.01)

(58) Field of Classification Search
CPC .. B29L 2023/00; B29L 2023/22; B65B 53/02; B65D 71/08; F16L 11/04; Y10T 428/1328
See application file for complete search history.

(56) References Cited

U.S. PATENT DOCUMENTS

| | | | |
|---|---|---|---|
| 4,399,181 A | 8/1983 | Yoshimura et al. |
| 4,403,794 A | 9/1983 | Curran et al. |
| 4,473,067 A | 9/1984 | Schiff |
| 4,842,918 A | 6/1989 | Ochiumi |
| 5,149,467 A | 9/1992 | Zarian |
| 5,317,061 A | 5/1994 | Chu et al. |
| 6,105,777 A | 8/2000 | Castellarin et al. |
| 6,187,130 B1 | 2/2001 | Berard et al. |
| 6,358,460 B1 | 3/2002 | Hunt, Jr. et al. |
| 6,454,744 B1 | 9/2002 | Spohn et al. |
| 6,632,541 B2 | 10/2003 | Johoji et al. |
| 6,663,595 B2 | 12/2003 | Spohn et al. |
| 6,702,972 B1 | 3/2004 | Markle |
| 6,852,261 B2 | 2/2005 | Benjamin |
| 6,863,757 B1 | 3/2005 | Gonzalez et al. |
| 6,863,852 B1 | 3/2005 | Ballard et al. |
| 7,344,765 B2 | 3/2008 | Hayakawa et al. |
| 7,637,902 B2 | 12/2009 | Eversull et al. |
| 7,678,223 B2 | 3/2010 | Strong et al. |
| 7,815,762 B2 | 10/2010 | Lentz et al. |
| 7,837,671 B2 | 11/2010 | Eversull et al. |
| 8,048,034 B2 | 11/2011 | Eversull et al. |
| 8,216,498 B2 | 7/2012 | Quillin |
| 8,387,347 B2 | 3/2013 | Imai et al. |
| 8,696,974 B2 | 4/2014 | Moriuchi et al. |
| 8,723,404 B2 | 5/2014 | Masuda et al. |
| 9,440,044 B2 | 9/2016 | Roof et al. |
| 9,446,171 B2 | 9/2016 | Suzuki et al. |
| 9,464,149 B2 | 10/2016 | Suzuki et al. |
| 9,623,154 B2 | 4/2017 | Suzuki et al. |
| 9,901,661 B2 | 2/2018 | Roof et al. |
| 9,957,384 B2 | 5/2018 | Suzuki et al. |
| 10,434,222 B2 | 10/2019 | Roof et al. |
| 2001/0045257 A1 | 11/2001 | Pepin et al. |
| 2003/0114732 A1 | 6/2003 | Webler et al. |
| 2004/0230212 A1 | 11/2004 | Wulfman |
| 2005/0182387 A1 | 8/2005 | Webler |
| 2006/0233984 A1 | 10/2006 | Suzuki et al. |
| 2007/0020413 A1 | 1/2007 | Moriuchi et al. |
| 2008/0097580 A1 | 4/2008 | Dave |
| 2008/0169582 A1 | 7/2008 | Dave et al. |
| 2008/0248226 A1 | 10/2008 | Simon et al. |
| 2009/0069748 A1 | 3/2009 | Schaeffer |
| 2009/0258243 A1 | 10/2009 | Maruyama et al. |
| 2012/0021151 A1 | 1/2012 | Tatarka et al. |
| 2013/0253328 A1 | 9/2013 | Zelenka et al. |
| 2014/0255633 A1 | 9/2014 | Suzuki et al. |
| 2015/0080506 A1 | 3/2015 | Kurosaki |
| 2015/0352319 A1* | 12/2015 | Roof ................ B29C 66/40 428/34.9 |
| 2015/0354732 A1 | 12/2015 | Roof et al. |
| 2016/0058983 A1 | 3/2016 | Poker et al. |
| 2016/0222145 A1 | 8/2016 | Suzuki et al. |
| 2016/0317716 A1 | 11/2016 | Suzuki et al. |
| 2017/0058115 A1 | 3/2017 | Suzuki et al. |
| 2017/0095597 A1 | 4/2017 | Roof et al. |
| 2018/0193532 A1 | 7/2018 | Roof et al. |

FOREIGN PATENT DOCUMENTS

| | | |
|---|---|---|
| JP | H0386742 A | 4/1991 |
| JP | H03224723 A | 10/1991 |
| JP | 06-194283 A | 7/1994 |
| JP | H11323053 A | 11/1999 |
| JP | 2004123920 A | 4/2004 |
| JP | 2007-179889 A | 7/2007 |
| JP | 2007269913 A | 10/2007 |
| JP | 2007321817 A | 12/2007 |
| JP | 2008020037 A | 1/2008 |

* cited by examiner

PEELABLE HEAT-SHRINK TUBING

PRIORITY

This patent application claims priority to U.S. Provisional Patent Application No. 62/531,228, filed on Jul. 11, 2017 and entitled "PEELABLE HEAT-SHRINK TUBING," the entire disclosure of which is incorporated herein by reference.

TECHNICAL FIELD

The present invention relates generally to heat-shrink tubing, and more particularly, to heat-shrink tubing for the manufacture of catheters.

BACKGROUND

Heat-shrink tubing has been utilized in many different manufacturing processes, including the assembly of catheters. For example, catheter components (e.g., a mandrel, a metal coil, and one or more polymeric tubings) can be inserted into the heat-shrink tubing and form an assembly. The assembly can then be heated, causing the heat-shrink tubing to compress around the components of the catheter. This compression can inwardly urge an outer polymeric tubing toward to an inner polymeric tubing, encapsulating the metal coil. The heat-shrink tubing may then be removed and discarded.

OVERVIEW

The present inventors recognize that there is a need to improve features of existing heat-shrink tubing. For one, existing heat-shrink tubing does not provide sufficient visibility properties. Opaque heat-shrink tubing reduces visibility of inserted catheter components, making proper insertion and alignment of the components difficult. On the other hand, transparent tubing that is not itself visible makes its removal difficult. Furthermore, existing heat-shrink tubing is not peelable and requires full-length skiving. Skiving is a difficult process—it cannot be too much (over-skiving) or too little (under-skiving). In the case of over-skiving, the surface of the catheter can be damaged. In the case of under-skiving, the heat-shrunk tubing cannot be easily removed from the catheter or the skiving process needs to be repeated. In general, the skiving process requires well-trained and experienced operators. Accordingly, the present inventors recognize that there is need for an improved heat-shrink tubing for catheter assembly applications, which is peelable and has better visibility properties. The disclosed tubings and methods are directed to mitigating or overcoming one or more of these recognized problems.

A first embodiment of the present invention is directed to a peelable heat-shrink tubing. The peelable heat-shrink tubing may include a base polymer comprising fluorinated ethylene propylene (FEP), and at least one fluoropolymer coextruded with the base polymer. The peelable heat-shrink tubing may have a total luminous transmittance between about 70% and 85%, inclusive.

A second embodiment of the present invention is directed to a peelable heat-shrink tubing. The peelable heat-shrink tubing may include a base polymer comprising fluorinated ethylene propylene (FEP), and at least one fluoropolymer coextruded with the base polymer. The peelable heat-shrink tubing may have an absolute value of in-plane birefringence less than about 0.001, inclusive.

In some embodiments, the total luminous transmittance of the peelable heat-shrink tubing may be less than about 80%.

In some embodiments, the peelable heat-shrink tubing may be quasi-isotropic.

In some embodiments, the base polymer may include FEP NP-130, and the at least one fluoropolymer may include ethylene tetrafluoroethylene (ETFE).

In some embodiments, the base polymer may constitute between about 87.5% and 92.5% by composition of the peelable heat-shrink tubing, inclusive, and the at least one fluoropolymer may constitute between about 7.5% and 12.5% by composition of the peelable heat-shrink tubing, inclusive.

In some embodiments, the FEP N-130 may constitute between about 87.5% and 92.5% by composition of the peelable heat-shrink tubing, inclusive, and the ETFE may constitute between about 7.5% and 12.5% by composition of the peelable heat-shrink tubing, inclusive.

In some embodiments, the peelable heat-shrink tubing may include 87.5% of FEP N-130 and 12.5% of ETFE, each by composition of the heat-shrink tubing.

In some embodiments, the peelable heat-shrink tubing may include 87.5% of FEP N-130, 7.5% of ETFE, and 5% of perfluoroalkoxyl alkane (PFA), each by composition of the peelable heat-shrink tubing.

In some embodiments, the peelable heat-shrink tubing may have a reduction ratio between about 1.30:1 and 1.84:1, inclusive.

In some embodiments, the peelable heat-shrink tubing may have a reduction ratio between about 1.65:1 and 1.84:1, inclusive.

In some embodiments, the peelable heat-shrink tubing may have an absolute value of out-of-plane birefringence less than about 0.050.

In some embodiments, the peelable heat-shrink tubing may have an absolute value of out-of-plane birefringence less than about 0.005.

In some embodiments, the peelable heat-shrink tubing may have a first melting peak temperature between about 245° C. and 255° C., inclusive.

In some embodiments, the peelable heat-shrink tubing may have a crystallization peak temperature between about 230° C. and 245° C., inclusive.

BRIEF DESCRIPTION OF THE DRAWINGS

In order that the invention may be readily understood, aspects of this invention are illustrated by way of examples in the accompanying drawings.

The same or similar reference numbers are used in the drawings and the following Detailed Description to refer to the same or similar parts.

DETAILED DESCRIPTION

The invention will now be described with reference to the figures. The heat-shrink tubing may have a semi-transparent appearance, allowing visibility of inserted catheter components and of the heat-shrink tubing itself, even under the bright lighting of a manufacturing environment. The semi-transparent appearance may be determined by one or more of the diffuse transmittance percentage, the total luminous transmittance percentage, and/or the haze percentage. The heat-shrink tubing may also be peelable providing benefits to the manufacturing process of a catheter. The benefits may include simple operation, reduced training costs and time, no or reduced risk of damaging the catheter from skiving, and/or increased yield of the catheter. The heat-shrink tubing may further have low in-plane birefringence and/or low out-of-plane birefringence.

Figure 1:
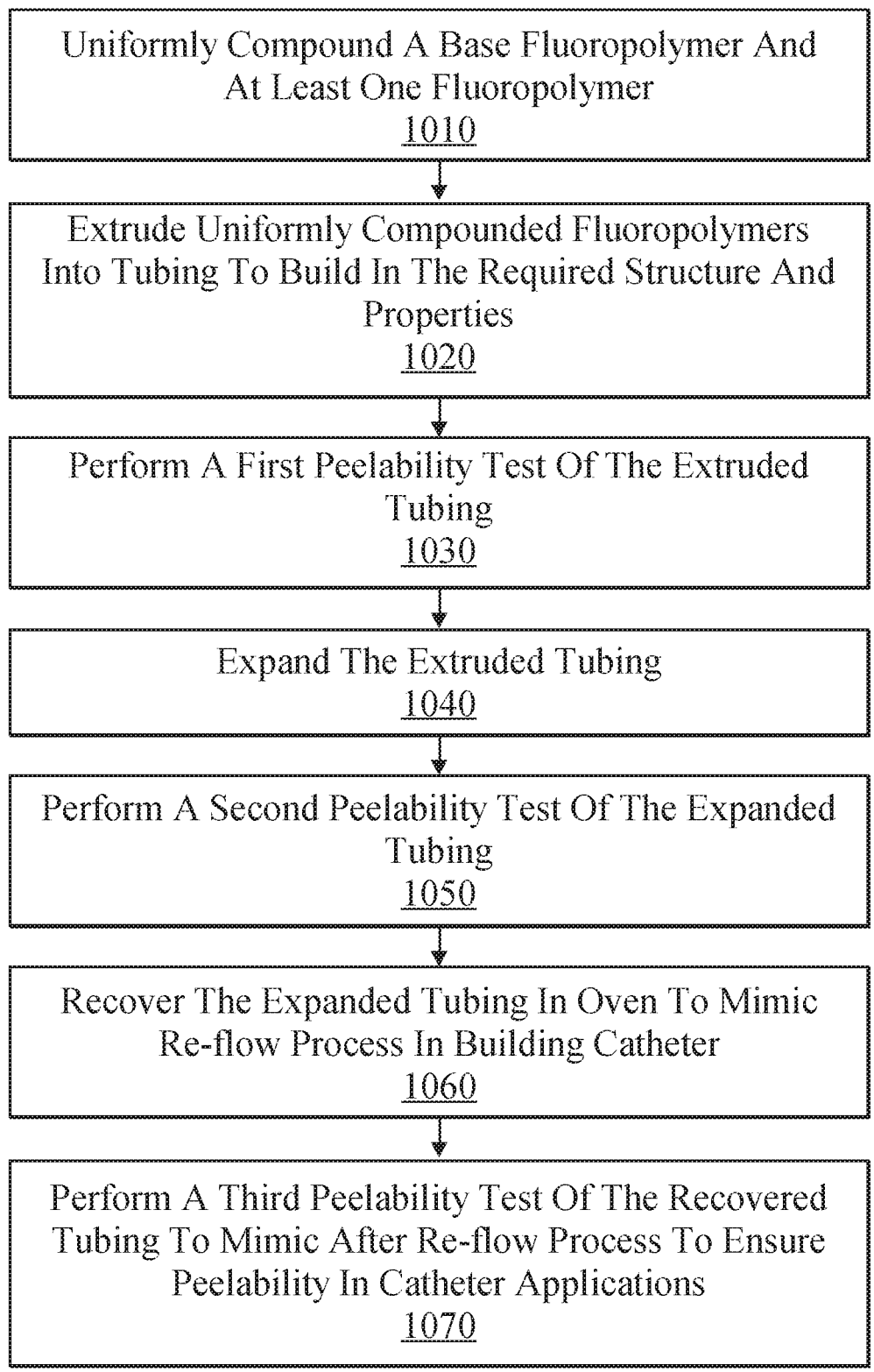
FIG. 1 illustrates a method of manufacturing an exemplary heat-shrink tubing according the present invention.

FIG. 1 illustrates a method of manufacturing a heat-shrink tubing. The peelability of the heat-shrink tubing may be tested at various stages, including after extruding the tubing, after expanding the tubing, and/or after recovering the tubing. The manufacturing parameters may be adjusted based on results of the peelability testing.

Step 1010 may include uniformly compounding fluouropolymers. The fluoropolymers may include a base polymer of a homogeneous fluorinated ethylene propylene (FEP). The base polymer may be compounded with at least one fluoropolymer, including one or more of another type of FEP, perfluoroalkoxy alkanes (PFA), ethylene chlorotrifluoroethylene (ECTFE), ethylene tetrafluoroethylene (ETFE), polychlorotrifluoroethene (PCTFE), and ethylene fluorinated ethylene propylene (EFEP). Therefore, the peelable heat-shrink tubing may include two or more different fluoropolymers. For example, in some embodiments, the peelable heat-shrink tubing may include a composition of between about 87.5% and 92.5% of a base polymer of Daikin FEP NP-130, inclusive, and between about 7.5% and 12.5% of Chemours ETFE Tefzel 750, inclusive. In some embodiments, the peelable heat-shrink tubing may have a composition including about 87.5% Daikin FEP NP-130, about 7.5% Chemours ETFE Tefzel 750, and about 5% PFA. The compounding of the fluoropolymers may be performed by a twin-screw, which provides excellent mixing and uniform distribution of the fluoropolymers in the compound.

Step 1020 may include extruding the uniformly compounded fluoropolymers into tubing to build in the tubing's structure and properties by a single-screw melt extruder. In some embodiments, the compounded fluoropolymers may be melt extruded by a single-screw extruder.

Step 1030 may include performing a first peelability test of the extruded tubing.

Step 1040 may include expanding the extruded tubing.

Step 1050 may include performing a second peelability test of the expanded tubing.

Step 1060 may include recovering the expanded tubing in an oven to mimic a re-flow process in building of a catheter.

Step 1070 may include performing a third peelability test of the recovered tubing to mimic after a re-flow process to ensure peelability in catheter applications.

The heat-shrink tubing may have a quasi-isotropic structure. For example, the heat-shrink tubing may have low in-plane birefringence ($\Delta n_{12}$) and/or low out-of-plane birefringence ($\Delta n_{13}$), as illustrated in Table 1. Each of the birefringences ($\Delta n_{12}$, $\Delta n_{13}$) may be determined by a difference in refractive indexes between two directions in the sample. As illustrated below, both birefringences ($\Delta n_{12}$, $\Delta n_{13}$) may be near zero at the expanded stage. After recovery of the expanded tubings, the birefringence may be kept at low values even though the inner diameter, outer diameter, and wall thickness of the tubings have changed. In contrast, a control version of prior art homogenous FEP heat-shrink tubing has a relatively high birefringence, up to about 98 times greater than the samples of the presently disclosed tubing. After expansion, the birefringence of the control still has a high value even though the dimensions have changed. The low birefringence is derived from the selection of the compounded fluoropolymers and/or processing. As illustrated in Table 1, the absolute value of the in-plane birefringence ($\Delta n_{12}$) may be less than about 0.001 and/or the absolute value of the out-of-plane birefringence ($\Delta n_{13}$) may be less than about 0.050. In some embodiments, the absolute value of the out-of-plane birefringence ($\Delta n_{13}$) may be less than about 0.005

TABLE 1

| | Expanded Tube | | | After Recovery | | | | | |
|---|---|---|---|---|---|---|---|---|---|
| Sample | Wall Thickness (inch) | $\Delta n_{12}$ | $\Delta n_{13}$ | Wall Thickness (inch) | $\Delta n_{12}$ | $\Delta n_{13}$ | Reduction Ratio | Change of $\Delta n_{12}$ | Change of $\Delta n_{13}$ |
| 34A | NA | NA | NA | 0.0131 | −0.0008 | −0.0154 | 1.65:1 | NA | NA |
| 34B | 0.0071 | −0.0001 | 0.0002 | 0.0078 | 0.0001 | 0.0020 | 1.72:1 | 0.0002 | 0.0018 |
| 34C | 0.0072 | 0.0001 | 0.0005 | 0.0106 | 0.0001 | −0.0084 | 1.68:1 | 0.0000 | −0.0005 |
| Control | 0.0098 | 0.0098 | −0.0338 | 0.0136 | 0.0022 | −0.0084 | 1.66:1 | −0.0076 | 0.0254 |

Birefringence may be measured by Gaertner Polariscope Birefringence Measurement System including a collimator, a viewing telescope, an analyzer, a Babinet compensator, a polarizer adjustment, and a white light source with a predominant wavelength of 565 nm. Testing may be performed at room temperature. Before the measurements, the samples can be cut in the extruded direction to open the samples and followed by cold pressing to remove some curvature at a pressure of 5 kPa for 24 hours. The thickness of each sample can be measured by caliper.

The in-plane birefringence ($\Delta n_{12}$) and/or the out-of-plane birefringence ($\Delta n_{13}$) may be calculated based on Equations (1), (2), and (3), where the subscript 1 indicates the machine direction (MD) or extrusion direction, the subscript 2 indicates the traverse direction (TD), and the subscript 3 indicates the normal direction (ND). Ro is the material reading at 0°, and $R_\varphi$ is the material reading at an angle from 15° to 45° in 5° intervals. λ is the wavelength (565 nm), d is the thickness of the sample, n is the refractive index (1.344), and N is the number of test angles.

$$\Delta n_{12} = \frac{\lambda}{d} R_o \quad (1)$$

$$\Delta n_{13-\phi} = \frac{\lambda}{d} \left[ \frac{R_o - R_\phi \left(1 - \frac{\sin^2\phi}{n^2}\right)^{1/2}}{\frac{\sin^2\phi}{n^2}} \right] \quad (2)$$

$$\Delta n_{13} = \frac{\sum_i^N \Delta n_{13-\phi}}{N} \quad (3)$$

Figure 2:
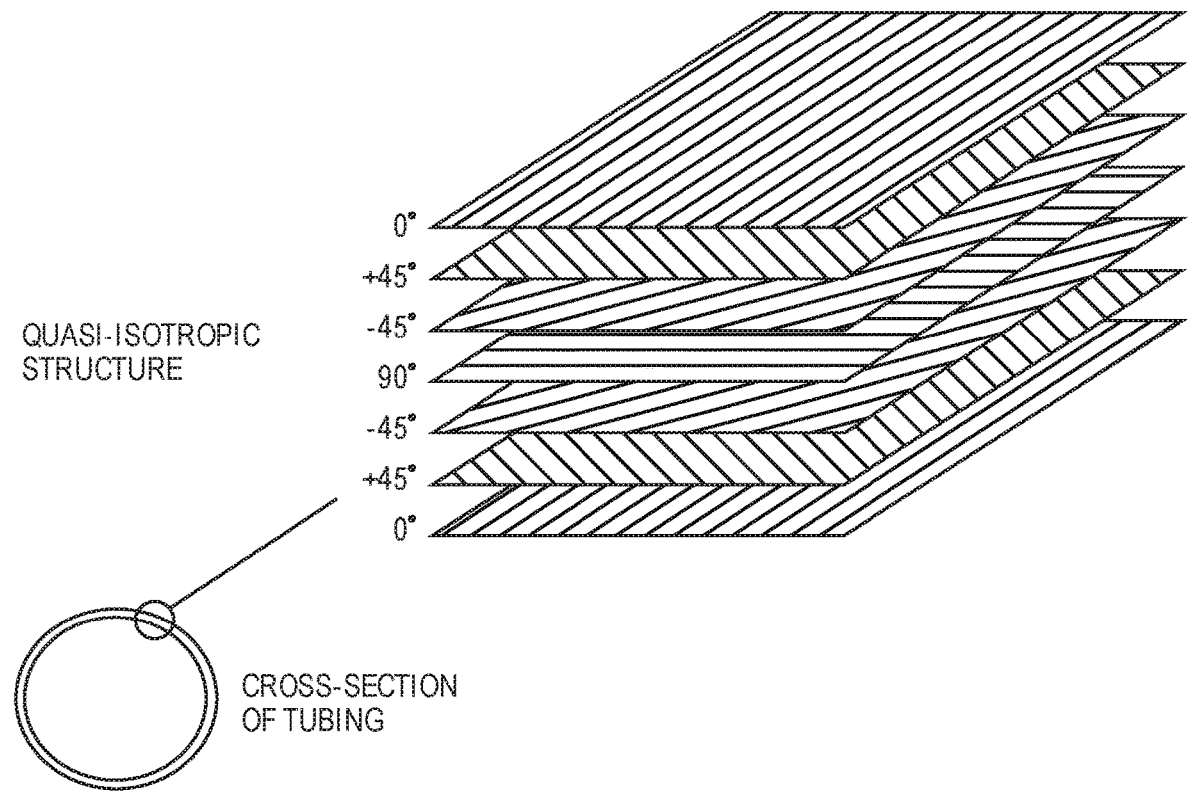
FIG. 2 illustrates a model of mechanical structure of the exemplary heat-shrink tubing of FIG. 1.

FIG. 2 illustrates a model of the quasi-isotropic structure of the heat-shrink tubing, based on the birefringence data.

The quasi-isotropic structure includes layers of different orientations and provides the peelability and low birefringence of the tubing. In contrast to a unidirectional structure, the tubings built with this cross-plied quasi-isotropic structure have a near zero net orientation. The range of birefringence depends on the combination of the layered structure. Furthermore, the tubings may have peelability because of the layers built with 0° fibers along the tubing or extrusion direction. Once an incision is introduced on one end of the tubing, the tubing can be continuously peeled in a longitudinal direction.

The reduction ratio illustrated in Table 1 may be determined by the ratio of the expanded inner diameter to the recovered inner diameter of the tubing. The expanded tubing can be introduced in an oven set at a constant temperature of 410° F. for 10 minutes, for example, to let the expanded tube be completely shrunk. The reduction ratio of the tubing may be about 1.30:1 to 2.00:1, inclusive. In some embodiments, the reduction ratio may be about 1.30:1 to 1.84:1, inclusive. In some embodiments, the reduction ratio of the tubing may be about 1.65.1 to 1.84:1, inclusive.

The tubing may have a semi-clear optical appearance to allow visibility of the tubing and of components inserted into the tubing. The tubing and inserted components may be visible under the bright lighting of a manufacturing environment. As illustrated in Table 2, embodiments of the tubing may have a haze between about 40% and 80%, inclusive, a total luminous transmittance between about 70% and 85%, inclusive, and/or a diffuse transmittance between about 35% and 70%, inclusive. In some embodiments, the haze of the tubing may be about 50% to 70%, inclusive, and/or, the total luminous transmittance may be less than about 80%, such as about 77.5%.

TABLE 2

| Sample ID | Thickness (inch) | Haze (%) | Total Luminous Transmittance (%) | Diffuse Transmittance (%) |
|---|---|---|---|---|
| 1188-30B | 0.011 | 64.7 | 81.6 | 52.8 |
| 1188-24D | 0.011 | 82.2 | 83.9 | 69.2 |
| 1188-33 | 0.014 | 43.9 | 79.8 | 35.0 |
| 1188-34 | 0.014 | 53.4 | 76.3 | 40.7 |
| 1188-35 | 0.010 | 70.0 | 71.7 | 50.2 |

The composition of the peelable heat-shrink tubing may be optimized to provide the semi-clear appearance based on the diameter of the peelable heat-shrink tubing. For example, the percentage of additive may be varied depending on the diameter of the peelable heat-shrink tubing. This principle may be illustrated in the following working examples. For larger diameter tubing (e.g., inner diameter of 0.115" to 0.480"), the composition may include about 12.5% ETFE by composition to provide the semi-clear optical appearance (e.g., about 70% to 85% total luminous transmittance). The remaining composition may consist of 87.5% FEP. For smaller diameter tubing (e.g., inner diameter of 0.040" to 0.115"), ETFE may be reduced to between about 7.5% and about 10% by composition to provide the semi-clear optical appearance (e.g., about 70% to 85% total luminous transmittance). The remaining composition may consist of FEP or a mixture of FEP and 5% PFA, as discussed herein.

The tubing appearance to light may be measured by Haze and Luminous Transmittance of Transparent Plastics with ASTM D1003-13 Procedure A (Hazemeter Method) test method. The tubing samples can be cut and prepared like film shape and pre-conditioned at least 40 hours at 23° C.+/−2° C. and at 50%+/−10% RH before the test. CIE Illuminant C and BYK Haze-Gard can be used in the tests. The Haze may be determined according to Equation (4).

$$\text{Haze}(\%) = \frac{\text{Diffuse Transmittance}(\%)}{\text{Total Luminous Transmittance}(\%)} \quad (4)$$

The specific gravity and density of the tubing samples may be measured per ASTM D792 Method A. The samples can be pre-conditioned for at least 40 hours at 23° C.+/−2° C. and 50%+/−5% RH before the measurements. Water with a specific gravity of 0.9980 can be used as a weighting medium at a constant temperature of 21.2° C. As illustrated in Table 3, the samples may have a density in the range of about 2.03 to 2.09 g/cm³, inclusive.

TABLE 3

| Sample ID | Density (g/cm³) | STDEV |
|---|---|---|
| 1188-24A | 2.0637 | 0.0162 |
| 1188-24B | 2.0735 | 0.0010 |
| 1188-30 | 2.0858 | 0.0261 |
| 1188-33 | 2.0302 | 0.0414 |
| 1188-34A | 2.0685 | 0.0029 |
| 1188-34B | 2.0624 | 0.0101 |
| 1188-34C | 2.0710 | 0.0255 |
| 1188-35 | 2.0303 | 0.0023 |

The samples may be analyzed through Differential Scanning Calorimetry (DSC) with a TA Instrument Model DSC Q2000. Each specimen can be exposed to a heat-cool-heat cycle. The first heating scan can contain thermal events reflecting thermal/processing history. The controlled cooling can provide an established thermal history and allow determination of the transitions based on material properties in the second heating scan. The temperature range of each segment can be from 25° C. to 350° C. and at heating/cooling rates of 10° C./minute. A helium gas purge of 25 ml/minute can be used. The melting peak temperature ($T_m$) of each sample may be determined using the peak maximum from the data recorded in the second heating segment of the analysis. No glass transition temperature was observed in the DSC tested samples. A summary of the results is shown in the following Table 4.

TABLE 4

| | 1st Heating Cycle | | Cooling Cycle | |
|---|---|---|---|---|
| Sample ID | $T_{m, Peak}$ (° C.) | $T_{m, Onset}$ (° C.) | $T_{m, Peak}$ (° C.) | $T_{m, Onset}$ (° C.) |
| 1188-24A | 250.7 | 236.4 | 234.1 | 238.0 |
| 1188-24B | 250.3 | 242.6 | 234.7 | 238.1 |
| 1188-24D | 250.7 | 235.2 | 233.4 | 235.7 |
| 1188-30 | 250.3 | 234.7 | 234.8 | 241.9 |
| 1188-30B | 250.0 | 236.0 | 235.2 | 242.4 |
| 1188-33 | 250.0 | 238.3 | 236.0 | 239.2 |
| 1188-34A | 249.5 | 236.7 | 236.4 | 240.0 |
| 1188-34B | 251.3 | 238.8 | 235.6 | 239.4 |
| 1188-34C | 249.2 | 235.9 | 236.9 | 240.1 |
| 1188-35 | 248.9 | 237.0 | 235.8 | 239.5 |

As illustrated, the first melting peak temperature may be about 240° C. to 265° C., inclusive. In some embodiments, the first melting peak temperature may be about 245° C. to 255° C., inclusive. In some embodiments, the first melting peak temperature may be about 248° C. to 251° C., inclusive.

The melting peak temperature of the cooling cycle (crystallization peak temperature) may be between about 230° C. and 245° C., inclusive. In some embodiments, the melting peak temperature of the cooling cycle may be between about 233° C. and 235° C., inclusive.

The melting onset temperature may be about 230° C. to 250° C., inclusive. In some embodiments, the melting onset temperature may be about 232° C. to 244° C., inclusive. In some embodiments, the melting onset temperature may be about 238° C. to 244° C., inclusive.

DSC results show the thermal behavior of a polymer or tubing in response to its physical crystalline structures in the heating and cooling cycles. In general, a melting peak temperature and the shape of the scan curve indicate the crystalline structures of the tested sample in term of crystalline sizes and the distribution of the crystal sizes. The special formulas and uniformly compounded fluoropolymers along with special extrusion and expansion process conditions build in unique structural properties of the present peelable heat-shrink tubings.

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment.

Certain terms are used throughout this patent document to refer to particular features or components. As one skilled in the art will appreciate, different people may refer to the same feature or component by different names. This patent document does not intend to distinguish between components or features that differ in name but not in function.

The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.).

What is claimed is:

1. A peelable heat-shrink tubing comprising:
   a base polymer comprising fluorinated ethylene propylene (FEP); and
   at least one fluoropolymer coextruded with the base polymer,
   wherein the peelable heat-shrink tubing has a total luminous transmittance between about 70% and 85%, inclusive, and
   wherein the peelable heat-shrink tubing is guasi-isotropic having layers of different orientation.

2. The peelable heat-shrink tubing of claim 1, wherein the total luminous transmittance is less than about 80%.

3. The peelable heat-shrink tubing of claim 1, wherein the at least one fluoropolymer comprises ethylene tetrafluoroethylene (ETFE).

4. The peelable heat-shrink tubing of claim 3,
   wherein the base polymer constitutes between about 87.5% and 92.5% by composition of the peelable heat-shrink tubing, inclusive, and
   wherein the at least one fluoropolymer constitutes between about 7.5% and 12.5% by composition of the peelable heat-shrink tubing, inclusive.

5. The peelable heat-shrink tubing of claim 4,
   wherein the FEP constitutes between about 87.5% and 92.5% by composition of the peelable heat-shrink tubing, inclusive, and
   wherein the ETFE constitutes between about 7.5% and 12.5% by composition of the peelable heat-shrink tubing, inclusive.

6. The peelable heat-shrink tubing of claim 5,
   wherein the FEP constitutes about 87.5% by composition of the peelable heat-shrink tubing, and
   wherein the ETFE constitutes about 12.5% by composition of the peelable heat-shrink tubing.

7. The peelable heat-shrink tubing of claim 5,
   wherein the FEP constitutes about 87.5% by composition of the peelable heat-shrink tubing, and
   wherein the at least one fluoropolymer further comprises perfluoroalkoxy alkane (PFA), the ETFE constitutes about 7.5% by composition of the peelable heat-shrink tubing, and the PFA constitutes about 5% by composition of the peelable heat-shrink tubing.

8. The peelable heat-shrink tubing of claim 1, wherein the peelable heat-shrink tubing has a reduction ratio between about 1.30:1 and 1.84:1, inclusive.

9. The peelable heat-shrink tubing of claim 8, wherein the peelable heat-shrink tubing has a reduction ratio between about 1.65:1 and 1.84:1, inclusive.

10. The peelable heat-shrink tubing of claim 1, wherein the peelable heat-shrink tubing has an absolute value of in-plane birefringence less than about 0.001.

11. The peelable heat-shrink tubing of claim 1, wherein the peelable heat-shrink tubing has an absolute value of out-of-plane birefringence less than about 0.050.

12. The peelable heat-shrink tubing of claim 11, wherein the peelable heat-shrink tubing has an absolute value of out-of-plane birefringence less than about 0.005.

13. The peelable heat-shrink tubing of claim 1, wherein the peelable heat-shrink tubing has a first melting peak temperature between about 245° C. and 255° C., inclusive.

14. The peelable heat-shrink tubing of claim 1, wherein the peelable heat-shrink tubing has a crystallization peak temperature between about 230° C. and 245° C., inclusive.

15. A peelable heat-shrink tubing comprising:
    a base polymer comprising fluorinated ethylene propylene (FEP); and
    at least one fluoropolymer coextruded with the base polymer,
    wherein the peelable heat-shrink tubing has an absolute value of in-plane birefringence less than about 0.001.

16. The peelable heat-shrink tubing of claim 15, wherein the peelable heat-shrink tubing has an absolute value of out-of-plane birefringence less than about 0.050.

17. The peelable heat-shrink tubing of claim 16, wherein the peelable heat-shrink tubing has an absolute value of out-of-plane birefringence less than about 0.005.

* * * * *